United States Patent
Nam et al.

(10) Patent No.: US 9,540,378 B2
(45) Date of Patent: Jan. 10, 2017

(54) COMPOSITION COMPRISING PURINE DERIVATIVES OR SALT THEREOF FOR PREVENTING OR TREATING ATOPIC DERMATITIS

(71) Applicant: DAEWOONG CO., LTD., Gyeonggi-do (KR)

(72) Inventors: Gyeong-Sug Nam, Gyeonggi-do (KR); Se-Joon Yoon, Seoul (KR); Ok-Gyung Choi, Gyeonggi-do (KR); Jin-Pyo Kim, Daejeon (KR); Soo-Jin Choi, Gyeonggi-do (KR); Hyong-Jin Park, Gangwon-do (KR)

(73) Assignee: DAEWOONG CO., LTD., Gyeonggi-do (KR)

( * ) Notice: Subject to any disclaimer, the term of this patent is extended or adjusted under 35 U.S.C. 154(b) by 4 days.

(21) Appl. No.: 14/394,414

(22) PCT Filed: Apr. 12, 2013

(86) PCT No.: PCT/KR2013/003062
§ 371 (c)(1),
(2) Date: Oct. 14, 2014

(87) PCT Pub. No.: WO2013/154373
PCT Pub. Date: Oct. 17, 2013

(65) Prior Publication Data
US 2015/0079157 A1    Mar. 19, 2015

(30) Foreign Application Priority Data

Apr. 13, 2012    (KR) .......................... 10-2012-0038305

(51) Int. Cl.
| | |
|---|---|
| *A61K 8/02* | (2006.01) |
| *C07D 473/18* | (2006.01) |
| *A61K 8/49* | (2006.01) |
| *A61K 9/00* | (2006.01) |
| *A61Q 19/00* | (2006.01) |
| *A61K 31/522* | (2006.01) |
| *A61K 47/44* | (2006.01) |

(52) U.S. Cl.
CPC ........... *C07D 473/18* (2013.01); *A23L 33/105* (2016.08); *A61K 8/4953* (2013.01); *A61K 9/0014* (2013.01); *A61K 31/522* (2013.01); *A61K 47/44* (2013.01); *A61Q 19/00* (2013.01); *A23V 2002/00* (2013.01)

(58) Field of Classification Search
CPC ..... A61K 47/44; A23L 33/05; A23V 2002/00; A23V 2200/318; A23V 2250/21
See application file for complete search history.

(56) References Cited

U.S. PATENT DOCUMENTS

| | | |
|---|---|---|
| 5,736,549 A | 4/1998 | Beasley et al. |
| 5,863,921 A | 1/1999 | Beasley et al. |
| 6,376,501 B1 | 4/2002 | Isobe et al. |
| 7,960,397 B2 | 6/2011 | Szucova et al. |
| 2003/0191307 A1 | 10/2003 | Blumenkopf et al. |

FOREIGN PATENT DOCUMENTS

| | | | |
|---|---|---|---|
| KR | 10-2010-0005736 A | 1/2010 | |
| KR | 1020100005736 | * 1/2010 | ............. A61K 36/68 |
| KR | 10-2010-0122356 A | 11/2010 | |
| KR | 10-2010-0122357 A | 11/2010 | |
| KR | 10-2010-0122358 A | 11/2010 | |
| KR | 10-2010-0122359 A | 11/2010 | |
| KR | 10-1079221 B1 | 11/2011 | |

OTHER PUBLICATIONS

Atopic dermatitis, Retrieved from URL:<http://www.nlm.nih.gov/medlineplus/ency/imagepages/19323.htm>, Retrieved on [Jun. 20, 2015].*
Guanine, 1,9-dimethyl—Compound Summary (CID 123508), Pub Chem Compound, NCBI, NLM, NIH, 4 pages, available online at: http://pubchem.ncbi.nlm.nih.gov/summary/summary.cgi?cid=123508; retrieved Jun. 4, 2013.

* cited by examiner

*Primary Examiner* — Nannette Holloman
(74) *Attorney, Agent, or Firm* — Vorys, Sater, Seymour & Pease LLP; Mih Suhn Koh

(57) ABSTRACT

The present invention provides a pharmaceutical composition for preventing or treating atopic dermatitis comprising 2-amino-1,9-dimethylpurin-6-one or its pharmaceutically acceptable salt as an active ingredient. And also, the present invention provides a cosmetic composition for improving atopic dermatitis comprising 2-amino-1,9-dimethylpurin-6-one or its pharmaceutically acceptable salt; and a food (i.e., a functional food) for preventing or improving atopic dermatitis comprising 2-amino-1,9-dimethylpurin-6-one or its pharmaceutically acceptable salt.

8 Claims, 9 Drawing Sheets

COMPOSITION COMPRISING PURINE DERIVATIVES OR SALT THEREOF FOR PREVENTING OR TREATING ATOPIC DERMATITIS

TECHNICAL FIELD

The present invention relates to a composition for preventing or treating atopic dermatitis comprising a purine derivative or its salt. More specifically, the present invention relates to a pharmaceutical composition for preventing or treating atopic dermatitis comprising a purine derivative or its salt, which is newly isolated from *Cordyceps bassiana*. And also, the present invention relates to a cosmetic composition for improving atopic dermatitis comprising the purine derivative or its pharmaceutically acceptable salt; and a food (i.e., a functional food) for preventing or improving atopic dermatitis comprising the purine derivative or its pharmaceutically acceptable salt.

BACKGROUND ART

Atopic dermatitis is one of the chronic skin diseases, accompanied by dry skin, keratinization, itching, etc. 0.5 to 1% of the total populations, especially 5 to 10% of children, suffer from atopic dermatitis, and the patients thereof are increasing recently. In the sites affected by atopic dermatitis, the infiltration of immune-related cells, such as macrophages, mast cells, Th lymphocytes, etc., is significantly increased. The serum IgE level is highly increased in the atopic dermatitis patients, because the number of Th2 cells is increased and thus the Th2 cell-secreted cytokines such as IL-6 stimulate B lymphocytes, thereby promoting the IgE secretion. Therefore, atopic dermatitis is classified into a Th2-type skin disease, which is related to immune system abnormalities. Although atopic dermatitis causes a lot of economic damage along with physical and mental suffering to the patient, the specific remedy for treating atopic dermatitis was not yet reported. Drugs such as steroids, antihistamines, etc. are currently used as a therapeutic agent against atopic dermatitis. However, because the long-term use of these drugs induces serious side effects, there is a need for an alternative drug.

*Cordyceps* is one of the insect-parasitic fungi and belongs to the genus *Cordyceps*. It is known that about 300 species are currently distributed around the world. *Cordyceps* invades insect larvae, pupae, adults, etc., to kill the insect, and then forms fruit bodies and fruits using it as a host. *Cordyceps*, which has been known as a secret medicine for eternal youth and long life in China, is being widely used as an herbal medicine for the treatment of respiratory diseases such as asthma, hepatic disease such as jaundice, etc. Recently, extensive researches on the immune enhancing effect thereof are underway. There are literatures reporting that a *C. sinensis* extract, a *C. militaris* extract, and cordycepin (the major component of *Cordyceps*) function as an anti-inflammatory agent, in addition to as an immune regulator.

*C. bassiana*, a kind of *Cordyceps*, is an insect-parasitic fungus belonging to the order Lepidoptera. *C. bassiana* was firstly found in China and has been also found in Korea. *Beauveria bassiana*, one of the forms emerging during the life cycle of *C. bassiana*, has been used in the treatment of neurological disorders, cancer, skin infections, wounds, etc., from long time ago in China and Korea (Donguibogam). However, there has been no information on the efficacies of the fruit body of *C. bassiana*.

Meanwhile, Korean patent no. 10-1013061 has disclosed that a *C. bassiana* extract is useful for preventing and treating skin itching and atopic dermatitis. And also, Korean patent no. 10-1079221 has disclosed an improved process for preparing a *C. bassiana* extract, the process of which involves hot-water extraction of *C. bassiana*. In addition, there have been disclosed an anti-atopic functional cosmetic soap composition, an anti-atopic functional cosmetic composition, an anti-atopic functional food composition, and an anti-atopic functional ice cream composition (Korean patent no. 10-1104408, Korean patent publication nos. 10-2010-0122356, 10-2010-0122357, and 10-2010-0122359).

DISCLOSURE

Technical Problem

The present inventors performed various researches for isolating a single compound showing an inhibitory activity against atopic dermatitis from an extract of *Cordyceps bassiana*. Especially, the present inventors carried out analyses and activity evaluations on numbers of extraction fractions. Surprisingly, the present inventors have found that a purine derivative, which has not yet reported as a substance present in *Cordyceps bassiana*, has an excellent inhibitory activity against atopic dermatitis.

Therefore, it is an object of the present invention to provide a pharmaceutical composition for preventing or treating atopic dermatitis comprising the purine derivative as an active ingredient.

And also, it is an object of the present invention to provide a cosmetic composition for improving atopic dermatitis comprising the purine derivative.

And also, it is an object of the present invention to provide a food (i.e., a functional food) for preventing or improving atopic dermatitis comprising the purine derivative.

Technical Solution

In accordance with the present invention, there is provided a pharmaceutical composition for preventing or treating atopic dermatitis comprising a compound of Formula 1 or its pharmaceutically acceptable salt as an active ingredient:

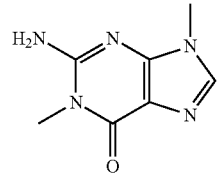

<Formula 1>

The pharmaceutical composition according to the present invention may have a dosage form for skin administration, for example, the dosage form selected from the group consisting of a solution, a gel, an emulsion, a suspension, a microemulsion, a microcapsule, a liposome, a cream, a lotion, an ointment, an aerosol, a spray, a paste, and a patch. In the pharmaceutical composition according to the present invention, the compound of Formula 1 may be present in an amount ranging from 0.005 to 0.5% by weight, based on the total weight of the composition.

And also, in accordance with the present invention, there is provided a cosmetic composition for improving atopic dermatitis comprising the compound of Formula 1 or its pharmaceutically acceptable salt. In the cosmetic composition according to the present invention, the compound of Formula 1 is present in an amount ranging from 0.005 to 0.5% by weight, based on the total weight of the composition.

And also, in accordance with the present invention, there is provided a functional food for preventing or improving atopic dermatitis comprising the compound of Formula 1 or its pharmaceutically acceptable salt. The functional food may have a powder form, a granular form, a tablet form, a capsule form, a syrup form, or a beverage form.

Advantageous Effects

It is newly found by the present invention that a purine derivative newly isolated from *Cordyceps bassiana* (i.e., the compound of Formula 1) has an excellent inhibitory activity against atopic dermatitis. Therefore, the pharmaceutical composition of the present invention comprising the compound of Formula 1 can be usefully applied for preventing or treating atopic dermatitis. And also, the cosmetic composition of the present invention comprising the compound of Formula 1 can be usefully used as cosmetics for improving atopic dermatitis, i.e., as anti-atopic functional cosmetics.

BEST MODE

Figure 1:
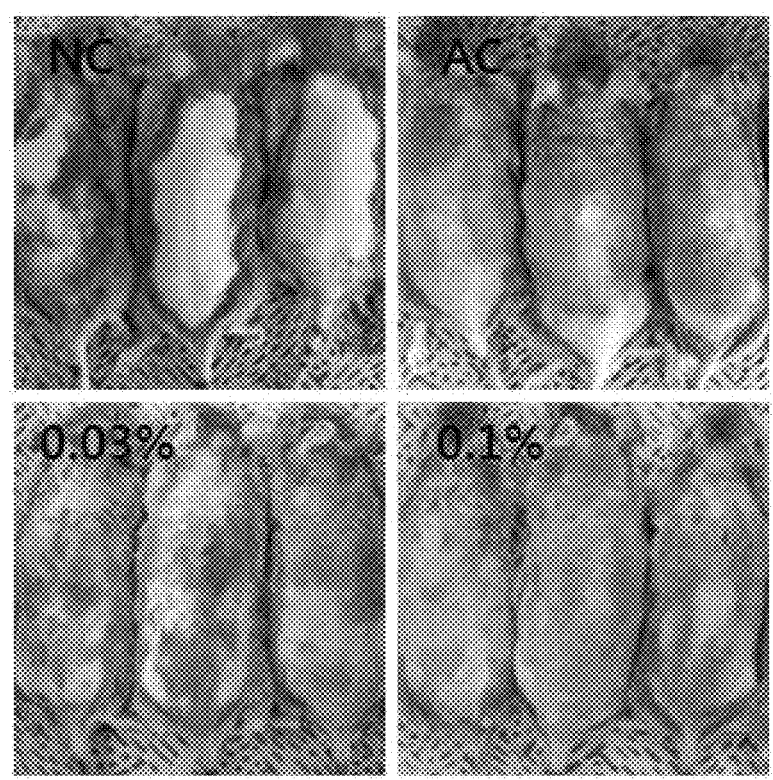
FIG. 1 shows the appearances of each test group mice after administering the compound of Formula 1 to the NC/Nga mice, animal models of atopic dermatitis, for 10 days. (NC: the normal control group, AC: the atopic control group, 0.03%: the test group treated with the compound of Formula 1 in the concentration of 0.03% by weight, 0.1%: the test group treated with the compound of Formula 1 in the concentration of 0.1% by weight)

As used herein, the term "atopic dermatitis", which is also referred to as atopic skin disease, includes all of the disorders accompanied thereby, such as dry skin, skin keratinization, skin itching, etc.

The present invention provides a pharmaceutical composition for preventing or treating atopic dermatitis comprising a compound of Formula 1 or its pharmaceutically acceptable salt as an active ingredient:

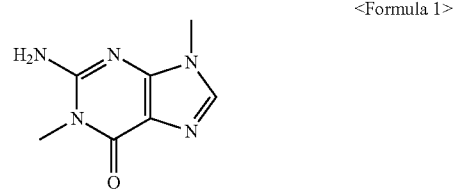

<Formula 1>

The present applicant obtained an extract of *Cordyceps bassiana* (CBW-Es) according to the methods disclosed in the present applicant's previous invention, i.e., Korean Patent no. 10-1079221. The extract was dissolved in alcohol such as methanol, followed by silica gel column chromatography. The resulting fractions were subject to a Prep-HPLC process, thereby isolating various compounds which have structural similarities to sugars and purine compounds. The present applicant isolated a single compound showing an excellent activity, through combination processes of solvent-recrystalization methods and structure-activity analyses thereon.

Structure analyses of the isolated compound were carried out, through spectrum data of UV, IR, H-NMR, C-NMR, EI-MS, etc. Surprisingly, it is found that the compound is a purine derivative which has not yet reported as a substance present in *Cordyceps bassiana*, i.e., 2-amino-1,9-dimethyl-purin-6-one having the above chemical structure of Formula 1. Although the compound of Formula 1 is a known compound (CAS 42484-34-4), there has been no report disclosing its pharmacological activity including atopic dermatitis. The compound of Formula 1 may be synthesized according to known methods in the art, e.g., Pierre R. LeBreton, Xu Yang, ShigeyukUrano, Sharon Fetzer, Min Yu, Nelson J. Leonardk Shiv Kumar, *J. Am. Chem. Soc.,* 1990, 112, 2138-2147. The compound of Formula 1 may be in various acid addition salt forms through the nitrogen atom therein, for example, an inorganic acid addition salt form such as hydrochloride, nitrate, sulfate, etc; and an organic acid addition salt form such as acetate, camphorsulfonate, citrate, etc.

The pharmaceutical composition of the present invention may comprise a pharmaceutically acceptable carrier, such as a diluent (e.g., lactose, corn starch, etc); a lubricant (e.g., magnesium stearate); an emulsifying agent; a suspending agent; a stabilizer; and/or an isotonic agent, which are conventionally used in the art. The pharmaceutical composition may be formulated to an oral dosage form or a parenteral dosage form, preferably to a parenteral dosage form, more preferably to a dosage form for skin administration, e.g., to a dosage form selected from the group consisting of a solution, a gel, an emulsion, a suspension, a microemulsion, a microcapsule, a liposome, a cream, a lotion, an ointment, an aerosol, a spray, a paste, and a patch. And also, the pharmaceutical composition of the present invention may be in the form of an aqueous solution containing pharmaceutically acceptable carriers, e.g., saline having a pH level of 7.4; and topically applied on the skin in a form of solution, suspension, emulsion, semi-solid, etc. If necessary, the pharmaceutical composition of the present invention may be formulated, through combining with whitening agents, humectants, antioxidants, UV absorbing agents, surfactants, thickening agents, aqueous media (e.g., water, alcohol, etc.), agents for skin nutrition, etc. In the pharmaceutical composition, the compound of Formula 1 may be present in an amount ranging from 0.005 to 0.5% by weight, preferably 0.03 to 0.3% by weight, based on the total weight of the composition, but not limited thereto.

The pharmaceutical composition of the present invention may be administered in an effective dose ranging from about 0.01 mg/kg to about 10 mg/kg per day to a subject patient suffering from various atopic dermatitises. The dosage may be conventionally changed according to the patient's age, weight, and symptom.

The present invention also provides a cosmetic composition for improving atopic dermatitis comprising the compound of Formula 1 or its pharmaceutically acceptable salt.

The cosmetic composition of the present invention comprises the compound of Formula 1 or its pharmaceutically acceptable salt; and the form thereof is not limited. That is, the form of the cosmetic composition of the present invention may be a conventional form, such as cream, packs, lotion, essence, cleansing water, foundation, makeup base, etc. The cosmetic composition may be formulated along with a conventional carrier used in the field of cosmetics, according to conventional methods. The compound of Formula 1 or its pharmaceutically acceptable salt may be present in an amount ranging, e.g., from 0.005 to 0.5% by weight, preferably from 0.03 to 0.3% by weight, based on the unit cosmetic composition. Of course, the amount used may be changed according to the severity of atopic dermatitis, etc.

The present invention also provides a functional food for preventing or improving atopic dermatitis comprising the compound of Formula 1 or its pharmaceutically acceptable salt.

The functional food of the present invention can be used as a health functional food. According to Article 6727 of Korean Health Functional Food law, the "health functional food" refers to a food which is produced and processed using a source or component that carries out good functions on the human body. The "function" refers to an intake purporting to attain good health effects, that is, a nutrient control with respect to the structure and function of the human body or a physiological operation.

The food composition of the present invention may include a conventional food additive. The conformity of the "food additive" is determined, as long as there are no other regulations, in consideration with the standard and criteria of the corresponding item according to the general rule of the food additives codex and general tests approved by Korea Food & Drug Administration. The items listed on the "food additives codex" include a chemically synthesized substance, such as ketone, glycine, potassium citrate, nicotinic acid, or cinnamic acid; natural additives, such as persimmon color, an extract of licorice, crystalline cellulose, caoliang color, or guar gum; or mixed formulation, such as sodium L-glutamate formulation, alkali additives for noodles, preservatives, or tar color formulation.

The functional food of the present invention may include the compound of Formula 1 in an amount of 0.01 to 95% by weight, preferably 1 to 80% by weight, based on total weight of the composition, in order to prevent and/or improve atopic dermatitis. In addition, in order to prevent and/or improve atopic dermatitis, the functional food may be produced and processed into a powder form, a granular form, a tablet form, a capsule form, a syrup form, a beverage form, etc.

For example, in order to produce a health functional food in a tablet form, a mixture of the compound of Formula 1, an excipient, a binder, a disintegrant, and other additives may be granulated using a conventional method, and then compression molding process is preformed with a lubricant. Alternatively, the mixture can be directly subjected to the compression molding process. In addition, when needed, the health functional food in a tablet form may include sweetening agents, and when needed, the health functional food in a tablet form can be coated with coating materials. Among health functional foods in a capsule form, a hard capsule formulation can be produced by filling a conventional hard capsule with a mixture of the compound of Formula 1 and an additive, such as an excipient, or granules of the mixture, or coated granules of the mixture; and a soft capsule formulation can be produced by filling a capsule support such as gelatin with a mixture of the compound of Formula 1 and an additive, such as an excipient. When needed, the soft capsule formulation can include plasticizer, such as glycerin or sorbitol, a coloring agent, and a preservative. A health functional food in a granular form can be produced by granulating a mixture of the compound of Formula 1, an excipient, a binder, and a disintegrant using a suitable method. When needed, the health functional food in a granular form may include a flavoring agent and a sweetening agent. The excipient, the binder, the disintegrant, the lubricant, the sweetening agent, and the flavoring agent used in the present invention can be defined as corresponding materials having the same or similar functions disclosed in references known in the art (The Korean pharmacopoeia review, Moonsungsa Publication Co., Korea Pharmaceutical University Association, Fifth edition, p 33-48, 1989).

The present invention will be described in further detail with reference to the following examples. These examples are for illustrative purposes only and are not intended to limit the scope of the present invention.

EXAMPLE 1

Evaluation of In Vivo Inhibitory Activity of the Compound of Formula 1 Against Atopic Dermatitis 1. Test Methods
(1) Induction of Atopic Dermatitis
NC/Nga mice (male, 6 weeks old), animal models of atopic dermatitis, were subject to complete hair removal of the back skin, and then left for 24 hours for healing the minute wounds on the skin. Atopic dermatitis was induced to the mice as follows. That is, a 0.2% solution of 2,4-DNFB (2,4-dinitrofluorobenzene) was prepared by dissolving in a mixed solvent of acetone and olive oil (3:1, v/v). The solution (150 µl) was applied on the hair-removed site of each mouse twice per week for 4 weeks, to induce atopic dermatitis.

(2) Administration of the Test Material

The normal control group (NC) was subject to only complete hair removal of the back skin. In case of the atopic dermatitis-induced atopic control group (AC), only Vaseline was applied on the hair-removed sites. In case of the atopic dermatitis-induced test groups, the mixtures of the compound of Formula 1 (0.3% by weight and 0.5% by weight) with Vaseline were respectively applied on the affected sites twice per day for 10 days. Each group includes 8 mice.

(3) Evaluation of Therapeutic Activity Against Atopic Dermatitis

The therapeutic activity against atopic dermatitis was evaluated through measuring dermatitis scores, epidermis thicknesses, left and right ear thicknesses, serum IgE levels, and numbers of mast cells.

The dermatitis scores were determined by observing the affected sites at the time when the treatments were completed, and then evaluating the visual changes such as erythema, bleeding, scab, etc., so as to yield the scores ranging from 1 to 10. From the resulting dermatitis scores, the inhibition ratio of each test group was calculated in comparison with the atopic control group.

Skin tissue was taken in a size of 1 cm×1 cm from the central area of each affected site, fixed with 10% formaldehyde solution, embedded in paraffin film, and then cut into a 4 μm section. Each tissue section was subject to hematoxylin-eosin (H&E) staining, and then observed with an optical microscope (×200, 5 sites per tissue) so as to calculate the epidermis thickness thereof.

The left and right ear thicknesses were measured with a digital vernier caliper, at the time when the test was started and at the time when the test was completed.

The serum IgE level was measured in the blood collected from the heart of each group mice, according to ELISA (Enzyme-linked immunosorbent assay) methods.

Skin tissue was taken in a size of 0.5 cm×1 cm from the central area of each affected site, fixed with IHC zinc fixative formalin-free solution, embedded in paraffin film, and then cut into a 4 μm section. Each tissue section was adhered on a slide coated with poly-L-lysine, followed by removing the paraffin and hydrating. Each resulting section was subject to toluidine blue staining, and then observed with an optical microscope (×200, 3 sites per tissue) so as to measure the number of mast cells.

All measurement values were calculated in mean±standard deviation. Statistical significances were determined with ANOVA. ≤5% is considered as being statistically significant.

2. Test Results

Figure 2:
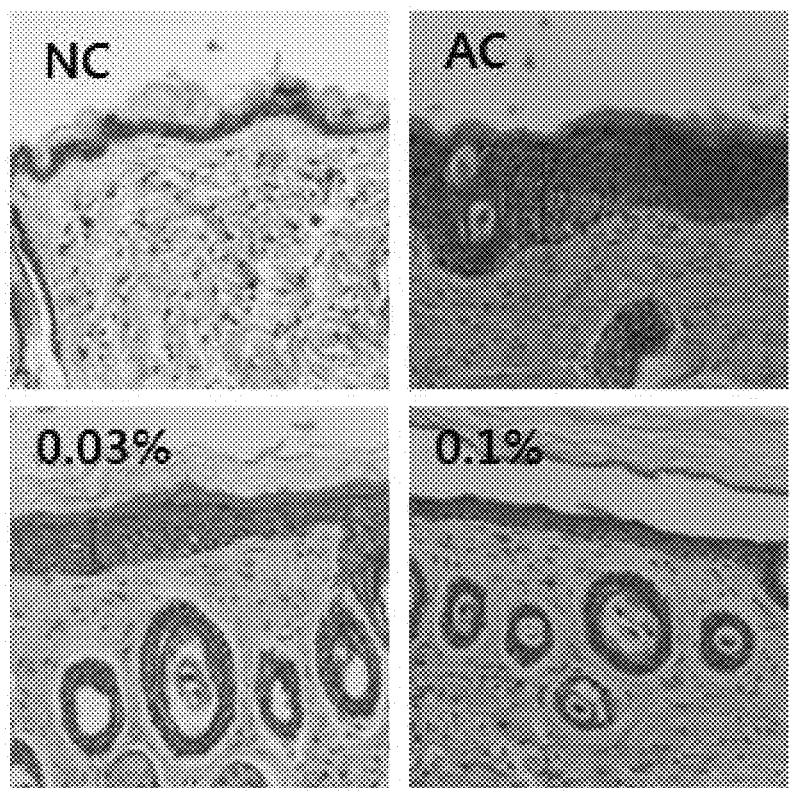
FIG. 2 shows the results obtained by staining the tissue sections derived from the affected skin tissues of the respective group mice with a hematoxylin-eosin (H&E) staining method, after administering the compound of Formula 1 to the NC/Nga mice, animal models of atopic dermatitis, for 10 days. (NC: the normal control group, AC: the atopic control group, 0.03%: the test group treated with the compound of Formula 1 in the concentration of 0.03% by weight, 0.1%: the test group treated with the compound of Formula 1 in the concentration of 0.1% by weight)
Figure 3:
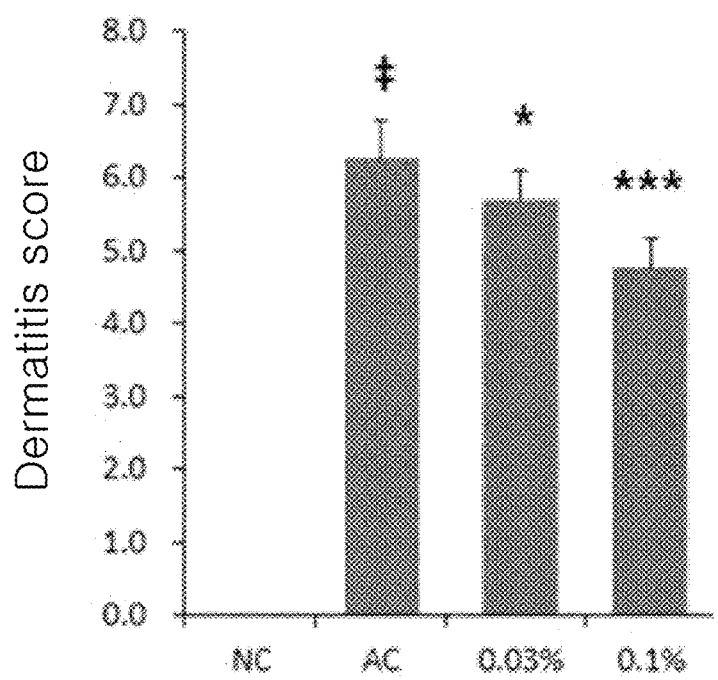
FIGS. 3 to 6 respectively show the results obtained by measuring dermatitis scores (FIG. 3), epidermis thicknesses (FIG. 4), differences of left and right ear thicknesses (FIG. 5), and serum IgE levels (FIG. 6) of each test group mice, after administering the compound of Formula 1 to the NC/Nga mice, animal models of atopic dermatitis, for 10 days. (NC: the normal control group, AC: the atopic control group, 0.03%: the test group treated with the compound of Formula 1 in the concentration of 0.03% by weight, 0.1%: the test group treated with the compound of Formula 1 in the concentration of 0.1% by weight)
Figure 4:
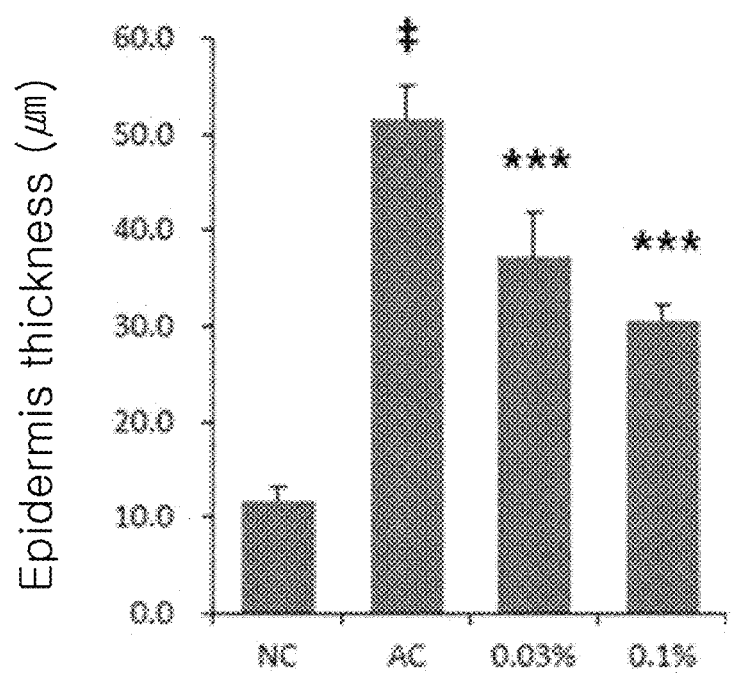
Figure 5:
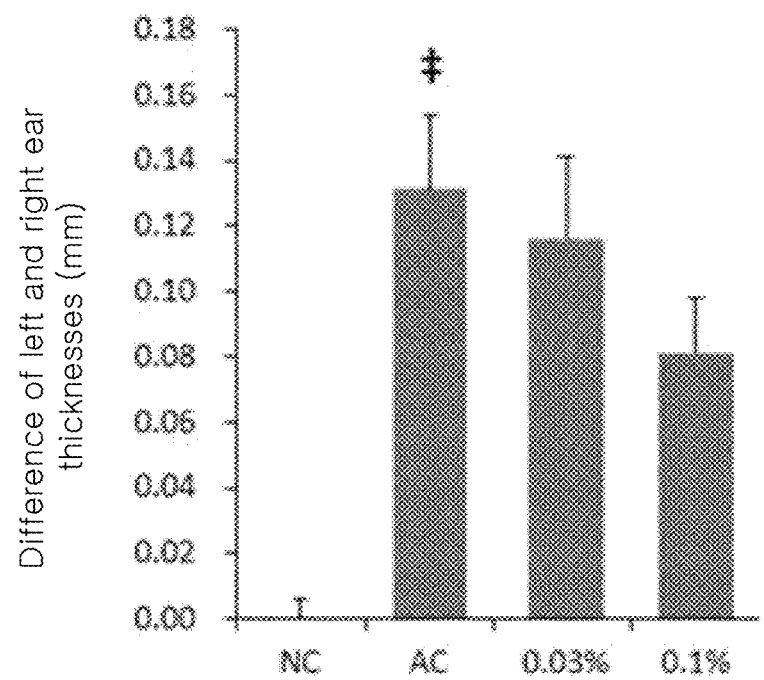
Figure 6:
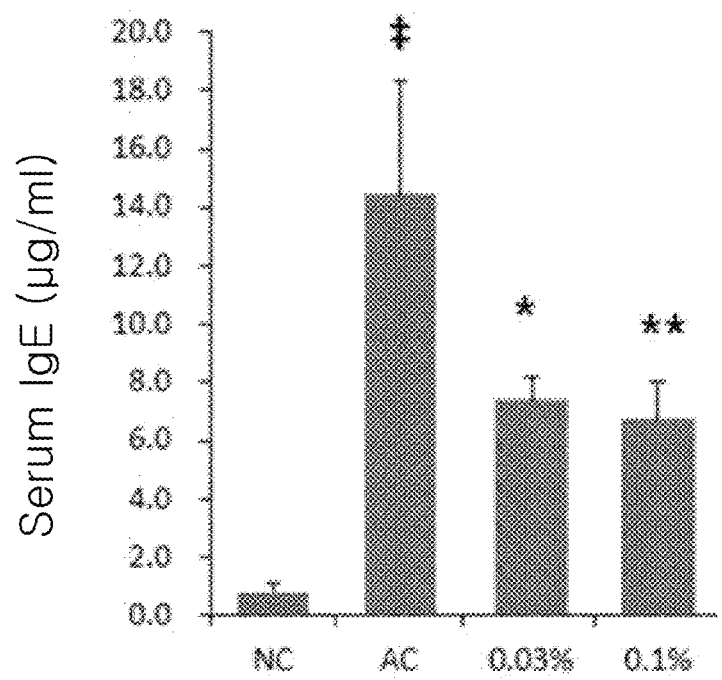
Figure 7:
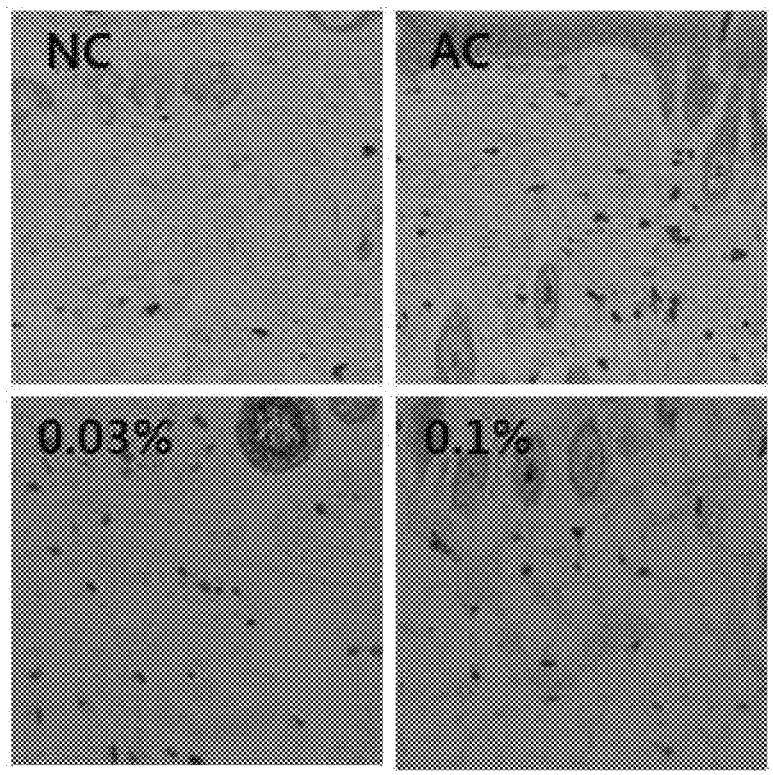
FIGS. 7 and 8 respectively show the results obtained by measuring the distributions of mast cells (FIG. 7) and the number of mast cells (FIG. 8) of each test group mice, after administering the compound of Formula 1 to the NC/Nga mice, animal models of atopic dermatitis, for 10 days. (NC: the normal control group, AC: the atopic control group, 0.03%: the test group treated with the compound of Formula 1 in the concentration of 0.03% by weight, 0.1%: the test group treated with the compound of Formula 1 in the concentration of 0.1% by weight)
Figure 8:
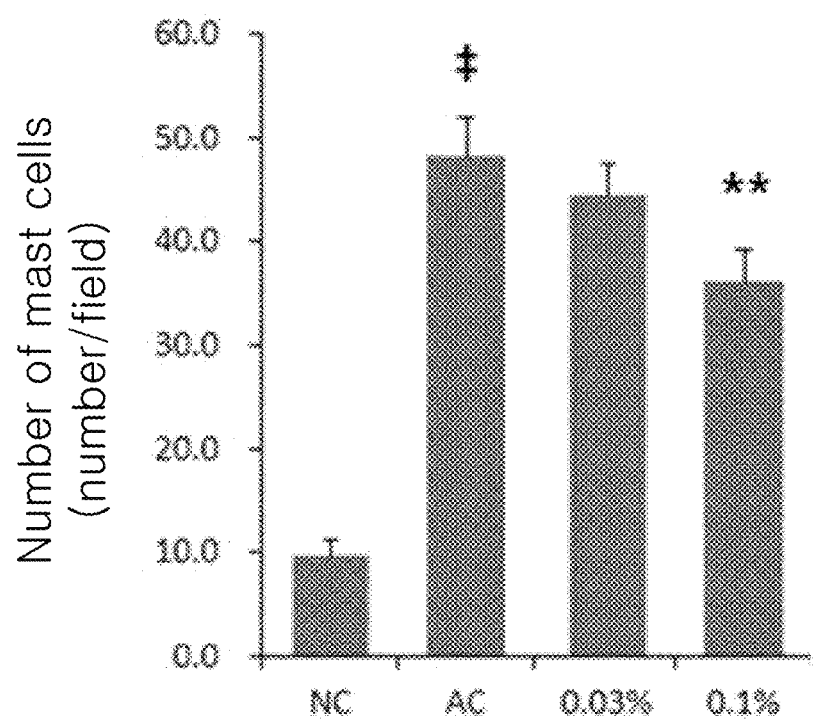

Each group of mice after the treatments for 10 days was shown in FIG. 1. The H&E staining results of the tissue sections obtained from each skin tissue were shown in FIG. 2. The results obtained by measuring dermatitis scores, epidermis thicknesses, differences of left and right ear thicknesses, and serum IgE levels were shown in FIGS. 3 to 6, respectively. The distributions of mast cells were shown in FIG. 7, from which the numbers of mast cells were measured. The results thereof were shown in FIG. 8.

The results of FIGS. 3 to 8 are summarized in the following table 1. The values of the table 1 mean the reducing ratios (%) of each evaluation item, in comparison with the atopic control group (AC).

TABLE 1

| Reducing ratio (%) | Test group 1 | Test group 2 |
|---|---|---|
| Dermatitis score | 8.96* | 24.00*** |
| Epidermis thickness | 36.13*** | 52.63*** |
| Difference of left and right ear thicknesses | 7.69 | 38.46 |
| Serum IgE level | 51.76 | 56.46** |
| Number of mast cells | 7.7 | 24.9** |

*p < 0.05,
**p < 0.01,
***p < 0.001 (in comparison with the atopic control group)

As shown in FIGS. 1 to 8 and the table 1, when the compound of Formula 1 was applied on the affected sites in concentrations of 0.03% (Test group 1) and 0.1% (Test group 2) for 10 days after the induction of atopic dermatitis for 4 weeks, all of the dermatitis scores, epidermis thicknesses, differences of left and right ear thicknesses, serum IgE levels, and numbers of mast cells, which had been increased by atopic dermatitis, were significantly reduced.

EXAMPLE 2

Evaluation of Inhibitory Activity Against Inflammatory Cytokine Expression

The inhibitory activity of the compound of Formula 1 was evaluated against the expressions of inflammatory cytokines of atopic dermatitis, i.e., IL-6, IL-10, IL-12p40, and COX-2. Briefly, the Raw264.7 mouse macrophage cell line (ATCC TIB-71) (about 1×10$^6$ cells) was added into the each well of a 12-well plate and then incubated in a RPMI medium supplemented with 100 U/ml penicillin, 100 ug/ml streptomycin and 10% fetal bovine serum. The cells were treated with the compound of Formula 1 (400 uM) and LPS (1 ug/ml), and then incubated under the condition of 37° C., 5% $CO_2$ for 24 hours. The cells isolated from each group of the medium were treated with a Trizol reagent to extract the total RNA. Each cDNA was prepared according to the vendor's instruction, using a First strand cDNA synthesis kit (Fermentas). The resulting cDNAs (in the same amount for each cDNA) were subject to PCR amplification. The sense and antisense primers used were prepared according to the disclosures, i.e., Zhi-Qiang Chang et al., *J. Nutr. Sci. Vitaminol.*, 2011, 27, p 118-122, JiYeon Lee et al., *Biol. Pharm. Bull.*, 2007, 30(11), p 2043-2051, E. V. Maryukhnich et al., *Biol. Sci.*, 2007, 414, p 242-245. The PCR amplification was carried out, using a i-Master PCR kit (iNtRON), in the HiPi solution (20 ul) containing each cDNA, sense/antisense primers for the target proteins (IL-6, IL-10, IL-12p40, and COX-2), control group GAPDH primers, dNTP (250 uM), Tris-HCL (pH8.3) (10 mM), KCl (50 mM), and $NgCl_2$ (1.5 mM).

The PCR was performed as follows: 30 seconds at 94° C. (for denaturing), 30 seconds at 55~58° C. (for annealing), and 1 minute at 72° C. (for extension). The annealing temperatures and the cycle numbers for each primer set were 25 cycles at 55° for GAPDH; 25 cycles at 55° for IL-6; 25 cycles at 55° for IL-10; 30 cycles at 58° for IL-12p40; and 25 cycles at 55° for COX-2, respectively. The results obtained by measuring the mRNA expression level of each cytokine through RT-PCR were shown in FIG. 9.

Figure 9:
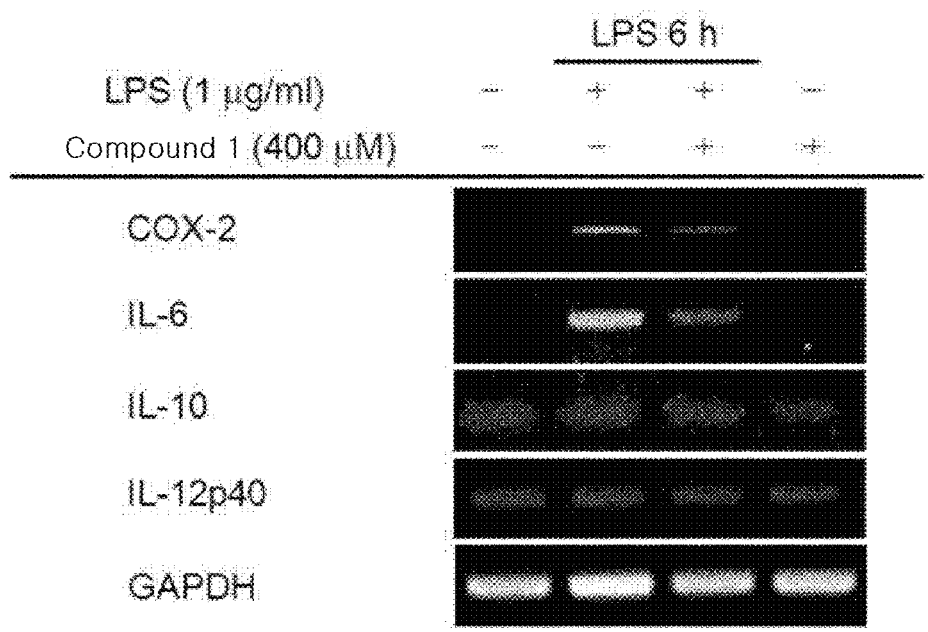
FIG. 9 shows the results obtained by measuring the mRNA expression levels of IL-6, IL-10, IL-12p40 and COX-2, which are known as inflammatory cytokines, when treating the LPS (lipopolysaccharide)-treated inflammation-induced Raw264.7 cells with the compound of Formula 1

As shown in FIG. 9, the compound of Formula 1 effectively inhibited the mRNA expression levels of COX-2, IL-6, IL-10, and IL-12p40, which are known as inflammatory cytokines of atopic dermatitis, in the LPS-treated inflammation-induced Raw264.7 cells. Therefore, it can be seen that the compound of Formula 1 inhibit atopic dermatitis in transcription level.

The invention claimed is:

1. A method for treating atopic dermatitis in a subject in need thereof comprising administering to the subject a pharmaceutical composition comprising an effective amount of an isolated compound of Formula 1 or its pharmaceutically acceptable salt as an active ingredient:

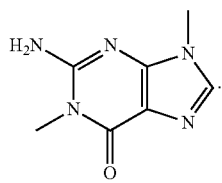

<Formula 1>

2. The method of claim 1, wherein the pharmaceutical composition is in a dosage form for skin administration.

3. The method of claim 2, wherein the dosage form is selected from the group consisting of a solution, a gel, an emulsion, a suspension, a microemulsion, a microcapsule, a liposome, a cream, a lotion, an ointment, an aerosol, a spray, a paste, and a patch.

4. The method of claim 1, wherein the effective amount of a compound of Formula 1 is an amount ranging from 0.005 to 0.5% by weight based on the total weight of the pharmaceutical composition.

5. A method for treating atopic dermatitis in a subject in need thereof comprising administering to the subject a cosmetic composition comprising an effective amount of an isolated compound of Formula 1 or its pharmaceutically acceptable salt as an active ingredient:

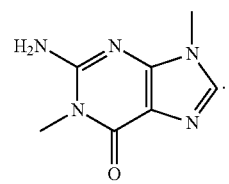

<Formula 1>

6. The method of claim 5, wherein the effective amount of a compound of Formula 1 is an amount ranging from 0.005 to 0.5% by weight based on the total weight of the composition.

7. A method for treating atopic dermatitis in a subject in need thereof comprising administering to the subject a functional food composition comprising an effective amount of an isolated compound of Formula 1 or its pharmaceutically acceptable salt as an active ingredient:

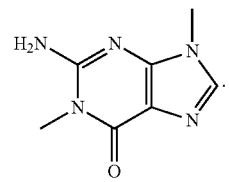

<Formula 1>

8. The method of claim 7, wherein the functional food composition is in a form selected from the group consisting of a powder form, a granular form, a tablet form, a capsule form, a syrup form, and a beverage form.

* * * * *